(12) United States Patent
De Oliveira

(10) Patent No.: US 6,403,654 B1
(45) Date of Patent: Jun. 11, 2002

(54) COMPOSITIONS FOR AND METHOD OF TREATMENT FOR PSORIASIS

(76) Inventor: Mariana De Oliveira, 788 Adelaide Street West, Toronto, Ontario (CA), M6J 1B4

( * ) Notice: Subject to any disclaimer, the term of this patent is extended or adjusted under 35 U.S.C. 154(b) by 0 days.

(21) Appl. No.: 09/548,754

(22) Filed: Apr. 13, 2000

(51) Int. Cl.⁷ .......................... A61K 47/32; A61K 35/78
(52) U.S. Cl. .................. 514/772.4; 514/863; 424/195.1
(58) Field of Search ........................ 424/401, 58, 195.1; 514/772.4, 861, 863, 864

(56) References Cited

U.S. PATENT DOCUMENTS 5,425,954 A * 6/1995 Thompson et al. ......... 424/401
6,027,716 A * 2/2000 Levin et al. .................. 424/58

* cited by examiner

Primary Examiner—Thurman K. Page
Assistant Examiner—Blessing Fubara
(74) Attorney, Agent, or Firm—Eugene J. A. Gierczak

(57) ABSTRACT

Improved compositions for treating psoriasis, including a body wash composition, spray composition and cream composition and the use of these novel compositions in a system or method of treating psoriasis.

20 Claims, No Drawings

COMPOSITIONS FOR AND METHOD OF TREATMENT FOR PSORIASIS

FIELD OF THE INVENTION

This invention relates in general to a treatment for psoriasis and more particularly to a medication for treating psoriasis having three different formulations, a system for using the medication, and a method of medical treatment.

BACKGROUND OF THE INVENTION

Psoriasis is a skin disorder that includes the presence of small elevations of the skin that may be characterized as elevated red lesions, plaques or pustules on the skin which eventually result in silvery scales. These silvery scales and plaque are the result of accelerated epidermal proliferation and the metabolic activity and proliferation of capillaries in the dermal region and the invasion of the dermis and epidermis by inflammatory cells. More specifically, the capillaries in the dermal region become tortuous and dilated as well as suffering an inflammatory reaction causing the skin to redden.

The exact mechanism which triggers the abnormal cell proliferation is not known, though it is believed there may be biochemical stimuli and environmental factors. The severity and course of psoriasis can vary greatly depending on the individual, but in general this chronic skin condition recurs throughout the life of the individual with varying intervals of one month to many years.

Over the years a wide variety of methods of treatment for psoriasis, both topical and systemic, which inhibit the cell division have been developed. In general, these methods have met with limited short term success and are not very well understood. As the disease requires treating the individual intermittently during their lifetime, treatment risk increases with treatment length since common medicaments evidence cumulative long term side effects.

Historically, psoriasis has been treated topically with coal tar derivatives as well as salicylic acid with limited success. Corticosteroids and other similar drugs have been found effective for serious cases of psoriasis. Unfortunately many of these drugs produce serious side effects, and in some cases once the drugs are discontinued, the psoriasis recurs with marked exacerbation. Other forms of treatment include folic acid antagonists, ionizing radiation therapy, a variety of combinations of ointments and polyethylene films, sunlight and ultraviolet baths.

Prior art psoriasis medications and methods of medical treatment have been devised to address the aforenoted problems. For example, U.S. Pat. No. 5,425,954 issued on Jun. 20, 1995 to Thompson et al. and provides for a composition for topical application to the skin comprising a mixture of Panthenol ($B_5$), Cod Liver Oil, Alpha Tocopherol Acetate, Arginine, Isoleucine, Leucine, Methionine, Phenylalanine, Threonine, and Valine in admixture with a suitable carrier.

U.S. Pat. No. 5,165,932 issued on Nov. 24, 1992 to Horvath and relates to therapeutical compositions on medical herb basis for the treatment of psoriasis and the preparation of the same. The medical herbs used in the invention are *Allium sativum*/garlic/, *Urtica dioica*/common nettle/, *Chelidonium majus*/milkweed/, *Veronica officinalis*/veronica/, *Calendula officinalis*/calendula or marigold/, *Achillea herba*/millefolium/yarrow/ and *Fumaria officinalis*/fumitory, earth-gall.

U.S. Pat. No. 4,981,681 issued on Jan. 1, 1991 to Tosti and relates to a method for treating psoriasis and more particularly it relates to a method of treating psoriasis by systematic and periodic application of several selected ingredients including the active ingredient Salicylic Acid.

U.S. Pat. No. 5,886,038 issued on Mar. 23, 1999 to Glenn et al. and relates to a pharmaceutical composition for use in the treatment of psoriasis, having isopropyl myristate as its only active ingredient.

U.S. Pat. No. 5,990,100 issued on Nov. 23, 1999 to Rosenbert et al. and this patent relates to pharmaceutical compositions and methods for use in the treatment of psoriasis, having isopropyl myristate as a first active ingredient and a different anti-psoriatic agent as a second active ingredient; preferably they are combined in the same pharmaceutical composition.

Thus a composition, system and method of treatment for psoriasis which allows for the successful treatment by reducing the frequency of the recurrence of the psoriasis is desirable.

SUMMARY OF THE INVENTION

An object of one aspect of the present invention is to provide improved compositions or pharmaceutical compositions for use in the treatment of psoriasis. A further object of the invention is to provide an improved system for treatment of psoriasis or method of medical treatment using novel compositions.

In accordance with one aspect of the present invention there is provided a composition for use in a psoriasis treatment comprising of an active agent wherein the active agent is coal tar and herbal extracts including mallow extract that may be mixed with a carrier mixture for topical administration.

In accordance with other aspects of the invention there are provided compositions for treating psoriasis that include a body wash composition, a spraying composition and a cream composition. Conveniently the active agents may include coal tar a variety of herbal extracts, including and mallow extract.

In accordance with another aspect of the invention there is provided a system for use in a psoriasis treatment that includes using a bathing composition, a spraying composition and a cream composition wherein the active agents include coal tar solution, herbal extracts including mallow extract in therapeutic effective doses and a carrier mixture for topical application.

In a final aspect of the present invention there is provided a method of treating psoriasis by topically administering to a human having psoriasis an effective amount of coal tar and herbal extracts including mallow extract, wherein the coal tar and herbal extract are present in a topically acceptable pharmaceutical bathing composition, spraying composition and cream composition.

DETAILED DESCRIPTION OF THE PREFERRED EMBODIMENT

The present invention relates to novel compositions and method of applying these compositions, which comprise of a selected mixture of herbal extracts and coal tar, which have the ability to reduce inflammation associated with psoriasis thereby encouraging healthy skin growth. The topical application of these novel compositions acts to treat skin, which has psoriasis. Topical application means the introduction of the novel compositions to the skin via a suitable base or vehicle. Conventional understanding of topical applications include but are not limited to creams, ointments, lotions, gels, pastes, powders, sprays, washes and the like.

The first novel composition of the present invention is comprised of the following essential herbal extracts and coal tar which have been formulated into a body wash composition, which has demonstrated in a reduction of inflammation associated with skin having psoriasis. Each of the components herein described is believed to contribute to the natural healing process of the psoriasis afflicted area although the exact mechanisms are not completely understood. The essential components of the novel body wash composition are: coal tar solution, mallow extract, rosemary oil, eucalyptus oil, a blend of proteins and wheat germ oil. The essential components are included in a suitable carrier for a body wash. More particularly a preferred composition of the body wash can contain a mixture of components that act as a carrier, the herbal extracts and coal tar in the following proportions given in weight percents as indicated in Table 1.

TABLE 1

Psoriasis Body Wash

| Substance | Percentage Range | Function |
|---|---|---|
| Water | 40.19–49.12 | Inert ingredient |
| Sodium Laureth Sulfate | 31.5–38.5 | Emulsifiers |
| Cocamide Dea | 4.5–5.5 | Thicker and foaming agent. Assists in removing fatty acids |
| Cocamidopropyl Betaine | 0.9–1.1 | Surfactant used as a cleanser. |
| Propylene Glycol | 0.27–0.33 | Cleanser |
| Citric Acid | 0.27–0.33 | PH Adjuster |
| Coal Tar Topical Solution | 5.4–6.6 | Active |
| Sodium Chloride | 1.8–2.2 | Thicker |
| Sodium Layroyl Sarcosinate | 1.8–2.2 | Cleansing |
| Wheat Germ Oil | 0.45–0.55 | Active |
| Blends of Proteins | 0.18–0.22 | Active |
| Methylchloroisothiazolinone | 0.045–0.055 | Preservative |
| Mallow Extract | 0.9–1.1 | Active |
| Rosemary Oil | 0.45–0.55 | Active |
| Eucalyptus Oil | 0.45–0.55 | Active/Counterirritant |
| Carbomer | 0.9–1.1 | Gelling Agent |

It will be apparent from the foregoing that the total percentage weight adds up to 100% and therefore the water component of the Psoriasis Body Wash will make up the remaining percentage after adding up the percentages of the remaining components.

Coal tar preparations have been approved for treating psoriasis and other skin problems such as dandruff. Coal tar is a byproduct of treated bituminous coal. Although long term exposure (20–25 years) to high concentrations of coal tar has been associated with skin cancer, topical compositions that are not used for long periods of time are considered fairly safe as the products are in contact with the skin for short periods of time.

Eucalyptus has antiseptic, cooling and stimulating properties. Rosemary is very rich in natural mineral and has soothing, cleansing, stimulating and astringent properties. Mallow has stimulating soothing properties associated with inflammation.

A second novel composition of the present invention is comprised of the following essential herbal extracts alone which have been formulated into a body spray composition, which has demonstrated in a reduction of inflammation associated with skin having psoriasis. Each of the components herein described is believed to contribute to the natural healing process of the psoriasis afflicted area although the exact mechanisms are not completely understood. The essential components of the novel body spray composition are: mallow extract, rosemary oil, and eucalyptus oil. More particularly a preferred composition of the body spray can contain a mixture of components that act as the carrier, herbal extracts in the following proportions given in weight percents as indicated in Table 2.

TABLE 2

Psoriasis Spray

| Substance | Percentage Range | Function |
|---|---|---|
| Water | 21.573–26.367 | Inert |
| Alcohol. | 63–77 | Inert |
| Sodium Iodide | 2.7–3.3 | Carrier |
| Potassium Iodide | 1.35–1.65 | Carrier |
| Sodium Thiosulphate | 0.027–0.033 | Neutralizer |
| Mallow Solution | 0.9–1.1 | Active |
| Rosemary Solution | 0.225–0.27 | Active |
| Eucalyptus Oil | 0.225–0.27 | Active |

A third novel composition of the present invention is comprised of the following essential herbal extracts and coal tar which have been formulated into a cream composition, which has demonstrated in a reduction of inflammation associated with skin having psoriasis. Each of the components herein described is believed to contribute to the natural healing process of the psoriasis afflicted area although the exact mechanisms are not completely understood. The essential components of the novel cream composition are: coal tar solution, mallow extract, chamomile extract, and tea tree solution. More particularly a preferred composition of the body cream can contain a mixture of components that act as a carrier, herbal extracts and coal tar solution in the following proportions given in weight percents as indicated in Table 3.

TABLE 3

Psoriasis Cream

| Substance | Percentage Range | Function |
|---|---|---|
| Water | 47.0205–57.4695 | Inert ingredient |
| Propylene Glycol | 3.6–4.4 | Cleanser |
| Mineral Oil | 2.7–3.3 | Oil Base |
| Cetyl Alcohol | 3.6–4.4 | Emulsifier |
| Stearic Acid | 3.6–4.4 | Emulsifier |
| Glycerol Monostearate | 2.7–3.3 | Emulsifier |
| F D & C Yellow #5 Solution | 0.045–0.055 | Colour |
| D & C Red #33 Solution | 0.0045–0.055 | Colour |
| Chamomile Extract | 0.9–1.1 | Active - Mineral |
| Carbomer | 3.6–4.4 | Gelling Agent |
| Methyl Paraben | 0.225–0.275 | Preservative |
| Propyl Paraben | 0.09–0.11 | Preservative |
| Triethanolamine | 0.54–0.66 | Emulsifier |
| Milk Amino Acids | 2.25–2.75 | Active |
| Tea Tree Solution | 2.7–3.3 | Active |
| Mallow Solution | 0.9–1.1 | Active |
| Coal Tar | 5.175–6.325 | Active |
| Dimethicone | 0.45–0.55 | Luster Agent |
| Glycerine | 2.7–3.3 | Humectant |
| Petrolatum | 0.9–1.1 | Emollient |
| Cetearyl Alcohol | 2.25–2.75 | Emollient/Thicker |
| Ceteareth 20 | 2.25–2.75 | Lubricant |
| Polysorbate 20 | 1.8–2.2 | Emulsifier |

The novel compositions may be used together as a system for use in a psoriasis treatment. More specifically, in operation, the user may apply the body wash composition to the area of skin that is affected with psoriasis. The body wash composition may be gently massaged into the affected area then rinsed with warm water and dried thoroughly. The novel body spray composition may be applied to the affected area and allowed to dry. Once the body spray has dried, the novel body cream may be applied to the affected area by massaging the body cream into the area. The system may be used on the affected area two to three times a day.

The novel compositions may each be used separately or in combination as a method of treating psoriasis comprising of topically administering to a human having psoriasis the novel body wash composition, the body spray composition or the body cream composition or a combination of the novel compositions.

The following Examples further illustrate various aspects of the invention.

EXAMPLE 1

In one particular example favourable results were observed by utilizing a Psoriasis Body Wash, Psoriasis Spray and Psoriasis Cream bearing the following specific percentage by weight (the specific numerical percentages relate to the specific components described earlier, for example, the second item 35.00 under Body Wash relates to 35% by volume of Sodium Laureth Sulfate, while the second item under Body Spray relates to 70% by weight alcohol and the second item under Body Cream relates to 4% by weight propylene glycol and so on) namely:

| Body Wash | | Body Spray | | Body Cream | |
|---|---|---|---|---|---|
| 44.65 | Water | 23.97 | Water | 52.245 | Water |
| 35.00 | Sodium Laureth Sulfate | 70.00 | Alcohol | 4.00 | Propylene Glycol |
| 5.00 | Cocamide Dea | 3.00 | Sodium Iodide | 3.00 | Mineral Oil |
| 1.00 | Cocamidopropyl Betaine | 1.50 | Potassium Iodide | 4.00 | Cetyl Alcohol |
| 0.30 | Propylene Glycol | 0.03 | Sodium Thiosulphate | 4.00 | Stearic Acid |
| 0.30 | Citric Acid | 1.00 | Mallow Solution | 3.00 | Glycerol Monostearate |
| 8.00 | Coal Tar Topical Solution | 0.25 | Rosemary Solution | 0.05 | F D & C Yellow #5 Solution |
| 2.00 | Sodium Chloride | 0.25 | Eucalyptus Oil | 0.005 | D & C Red #33 Solution |
| 2.00 | Sodium Layroyl Sarcosinate | | | 1.00 | Chamomile Extract |
| 0.05 | Wheat Germ Oil | | | 4.00 | Carbomer |
| 0.20 | Blends of Proteins | | | 0.25 | Methyl Paraben |
| 0.05 | Methylchloroisothiazolinone | | | 0.10 | Propyl Paraben |
| 1.00 | Mallow Extract | | | 0.60 | Triethanolamine |
| 0.5 | Rosemary Oil | | | 2.50 | Milk Amino Acids |
| 0.5 | Eucalyptus Oil | | | 3.00 | Tea Tree Solution |
| 1.00 | Carbomer | | | 1.00 | Mallow Solution |
| | | | | 5.75 | Coal Tar |
| | | | | 0.50 | Dimethicone |
| | | | | 3.00 | Glycerine |
| | | | | 1.00 | Petrolatum |
| | | | | 2.50 | Cetearyl Alcohol |
| | | | | 2.50 | Ceteareth 20 |
| | | | | 2.00 | Polysorbate 20 |

More particularly, by following the steps of:
(a) apply the body wash composition to the area of skin effected with psoriasis and gently massaging same to the effected area for a time period of up to ten minutes and then rinsing same with warm water and then drying same thereof;
(b) then apply the body spray of the specific composition referred to above to the effected area, and allowing same to dry;
(c) then apply the body cream having the specific composition referred to above; and
(d) repeating the steps two to three times a day.

By following the procedure referred to above, on observed a marked improvement over a span of one month where the area of skin showed a 50% reduction of psoriasis.

EXAMPLE 2

A 45 year old female patient with long standing psoriasis commenced treating her psoriasis by first applying the bodywash composition to the area of skin affected by psoriasis. The bodywash composition was gently massaged into the affected area was sprayed over the affected area and allowed to dry. Finally, the body cream was massaged into the affected area. The patient repeated this procedure in the morning and the evening over a period of 3–4 weeks. The patient's psoriasis cleared up almost completely, at the end of the 4 week period, with only small amounts of psoriasis periodically exhibiting on the patient's skin.

In summary, novel compositions for use in the treatment of psoriasis and corresponding system and method are provided for wherein the active agents are coal tar and a combination of herbal extracts including mallow.

Other variations and modifications of the invention are possible. All such modifications or variations are believed to be within the sphere and scope of the invention as defined by the claims appended hereto.

I claim:
1. A composition for use in a psoriasis treatment comprising active agents and a carrier mixture, wherein said active agents are at least five percent coal tar and a herbal extract in a therapeutic effective dose, wherein said herbal extract is selected from a group consisting of at least one percent mallow extract, rosemary extract and eucalyptus extract and said active agent mixes with said carrier mixture for administration of said composition.

2. A composition for treating psoriasis consisting of the following ingredients in the following percentage range by weight:
   (a) Water in the range of 40.19–49.12
   (b) Sodium laureth sulphate in the range of 31.5–38.5
   (c) Cocamide DEA in the range of 4.5–5.5
   (d) Cocamidopropyl betaine in the range of 0.9–1.1
   (e) Proylene glycol in the range of 0.27–0.33
   (f) Citric acid in the range of 0.27–0.33
   (g) Coal tar topical solution in the range of 5.4–6.6
   (h) Sodium chloride in the range of 1.8–2.2
   (i) Sodium layroyl sarcosinate in the range of 1.8–2.2
   (j) Wheat germ oil in the range of 0.45–0.55
   (k) Proteins (blends) in the range of 0.18–0.22
   (l) Methylchloroisothiazolinone in the range of 0.045–0.055
   (m) Mallow extract in the range of 0.9–1.1
   (n) Rosemary oil in the range of 0.45–0.55
   (o) Eucalyptus oil in the range of 0.45–0.55
   (p) Carbomer in the range of 0.9–1.1.

3. A composition for treating psoriasis consisting of the following ingredients in the following percentage range by weight:
   (a) Water in the range of 21.573–26.367
   (b) Alcohol in the range of 63–77
   (c) Sodium Iodide in the range of 2.7–3.3
   (d) Potassium iodide in the range of 1.35–1.65
   (e) Sodium thiosulphate in the range of 0.027–0.033
   (f) Mallow extract in the range of 0.9–1.1
   (g) Rosemary oil in the range of 0.225–0.27
   (h) Eucalyptus oil in the range of 0.225–0.27.

4. A composition for treating psoriasis consisting of the following ingredients in the following percentage range by weight:
   (a) Water in the range of 47.0205–57.4695
   (b) Propylene glycol in the range of 3.6–4.4
   (c) Mineral oil in the range of 2.7–3.3
   (d) Cetyl alcohol in the range of 3.6–4.4
   (e) Stearic acid in the range of 3.6–4.4
   (f) Glycerol monostearate in the range of 2.7–3.3
   (g) F D and C Yellow #5 solution in the range of 0.045–0.055
   (h) D and C red #33 solution in the range of 0.0045–0.055
   (i) Chamomile extract in the range of 0.9–1.1
   (j) Carbomer in the range of 3.6–4.4
   (k) Methyl paraben in the range of 0.225–0.275
   (l) Propyl paraben in the range of 0.09–0.11
   (m) Triethanolamine in the range of 0.54–0.66
   (n) Milk amino acids in the range of 2.25–2.75
   (o) Tea tree solution in the range of 2.7–3.3
   (p) Mallow extract in the range of 0.9–1.1
   (q) Coal tar topical solution in the range of 5.175–6.325
   (r) Dimethicone in the range of 0.45–0.55
   (s) Glycerine in the range of 2.7–3.3
   (t) Petrolatum in the range of 0.9–1.1
   (u) Cetearyl alcohol in the range of 2.25–2.75
   (v) Ceteareth 20 in the range of 2.25–2.75
   (w) Polysorbate 20 in the range of 1.8–2.2.

5. A pharmaceutical composition for use in the treatment of psoriasis comprising an anti-psoriatic agent selected from the group consisting of at least five percent coal tar solution and herbal extracts in an effective anti psoriatic percentage mixed with a carrier mixture for topical administration to a human.

6. A pharmaceutical composition for use in the treatment of psoriasis as claimed in claim 5 wherein said herbal extract is at least one percent mallow extract.

7. A system for use in a psoriasis treatment comprising a body wash composition, a spray composition and a cream composition, wherein said body wash composition, said spray composition and said cream composition further comprises an active agent and carrier mixture, wherein said active agent is at least five percent coal tar and at least one percent herbal extracts in a therapeutic effective dose, and said active agent mixes with said carrier mixture for administration of said body wash composition, said spray composition and said cream composition.

8. A system for use in a psoriasis treatment as claimed in claim 7 wherein said body wash composition consisting of the following ingredients in the following range of proportions based on weight:
   (a) Water in the range of 40.19–49.12
   (b) Sodium laureth sulphate in the range of 31.5–38.5
   (c) Cocamide DEA in the range of 4.5–5.5
   (d) Cocamidopropyl betaine in the range of 0.9–1.1
   (e) Proylene glycol in the range of 0.27–0.33
   (f) Citric acid in the range of 0.27–0.33
   (g) Coal tar topical solution in the range of 5.4–6.6
   (h) Sodium chloride in the range of 1.8–2.2
   (i) Sodium layroyl sarcosinate in the range of 1.8–2.2
   (j) Wheat germ oil in the range of 0.45–0.55
   (k) Proteins (blends) in the range of 0.18–0.22
   (l) Methylchloroisothiazolinone in the range of 0.045–0.055
   (m) Mallow extract in the range of 0.9–1.1
   (n) Rosemary oil in the range of 0.45–5.5
   (o) Eucalyptus oil in the range of 0.45–5.5
   (p) Carbomer in the range of 0.9–1.1.

9. A system for use in a psoriasis treatment as claimed in claim 7 wherein said spraying solution consisting of the following ingredients in the following range of proportions based on weight:
   (a) Water in the range of 21.573–26.367
   (b) Alcohol in the range of 63–77
   (c) Sodium Iodide in the range of 2.7–3.3
   (d) Potassium iodide in the range of 1.35–1.65
   (e) Sodium thiosulphate in the range of 0.027–0.033
   (f) Mallow extract in the range of 0.9–1.1
   (g) Rosemary oil in the range of 0.225–0.27
   (h) Eucalyptus oil in the range of 0.225–0.27.

10. A system for use in a psoriasis treatment as claimed in claim 7 wherein said cream composition consisting of the following ingredients in the following range of proportions:
    (a) Water in the range of 47.0205–27.4695
    (b) Propylene glycol in the range of 3.6–4.4
    (c) Mineral oil in the range of 2.7–3.3
    (d) Cetyl alcohol in the range of 3.6–4.4
    (e) Stearic acid in the range of 3.6–4.4

(f) Glycerol monostearate in the range of 2.7–3.3
(g) Coal tar topical solution in the range of 5.175–6.325
(h) Chamomile extract in the range of 0.9–1.1
(i) Methyl paraben in the range of 0.225–0.275
(j) Propyl paraben in the range of 0.09–0.11
(k) Triethanolamine in the range of 0.54–0.66
(l) Milk amino acids in the range of 2.25–2.75
(m) Mallow extract in the range of 0.9–1.1
(n) Tea tree solution in the range of 2.7–3.3
(o) Dimethicone in the range of 0.45–0.55
(p) Carbomer in the range of 3.6–4.4
(q) Glycerine in the range of 2.7–3.3
(r) Petrolatum in the range of 0.9–1.1
(s) Cetearyl alcohol in the range of 2.25–2.75
(t) Ceteareth 20 in the range of 2.25–2.75
(u) Polysorbate 20 in the range of 1.8–2.2
(v) F D and C Yellow #5 solution in the range of 0.045–0.055
(w) D and C red #33 solution in the range of 0.0045–0.055.

11. A method of treating psoriasis comprising topically administering to a human having psoriasis at least five percent coal tar and at least one percent herbal extract, said coal tar and herbal extract being present in a topically acceptable pharmaceutical body wash composition.

12. A method as claimed in claim 11 wherein said topically acceptable pharmaceutical bathing composition consisting of the following ingredients in the following range of proportions:
(a) Water in the range of 40.19–49.12
(b) Sodium laureth sulphate in the range of 31.5–38.5
(c) Cocamide DEA in the range of 4.5–5.5
(d) Cocamidopropyl betaine in the range of 0.9–1.1
(e) Proylene glycol in the range of 0.27–0.33
(f) Citric acid in the range of 0.27–0.33
(g) Coal tar topical solution in the range of 5.4–6.6
(h) Sodium chloride in the range of 1.8–2.2
(i) Sodium layroyl sarcosinate in the range of 1.8–2.2
(j) Wheat germ oil in the range of 0.45–0.55
(k) Proteins (blends) in the range of 0.18–0.22
(l) Methylchloroisothiazolinone in the range of 0.045–0.055
(m) Mallow extract in the range of 0.9–1.1
(n) Rosemary oil in the range of 0.45–0.55
(o) Eucalyptus oil in the range of 0.45–0.55
(p) Carbomer in the range of 0.9–1.1.

13. A method of treating psoriasis comprising topically administering to a human having psoriasis at least five percent coal tar and at least one percent herbal extract, said coal tar and herbal extract being present in a topically acceptable pharmaceutical spray composition.

14. A method for use in a psoriasis treatment as claimed in claim 13 wherein said topically acceptable pharmaceutical spraying composition consisting of the following ingredients in the following range of proportions:
(a) Water in the range of 21.573–26.367
(b) Alcohol in the range of 63–77
(c) Sodium Iodide in the range of 2.7–3.3
(d) Potassium iodide in the range of 1.35–1.65
(e) Sodium thiosulphate in the range of 0.027–0.033
(f) Mallow extract in the range of 0.9–1.1
(g) Rosemary oil in the range of 0.225–0.27
(h) Eucalyptus oil in the range of 0.225–0.27.

15. A method of treating psoriasis comprising topically administering to a human having psoriasis at least five percent coal tar and at least one percent herbal extract, said coal tar and herbal extract being present in a topically acceptable pharmaceutical cream composition.

16. A method of treating psoriasis as claimed in claim 15 wherein said topically acceptable pharmaceutical cream composition consisting of the following ingredients in the following range of proportions:
(a) Water in the range of 47.0205–27.4695
(b) Propylene glycol in the range of 3.6–4.4
(c) Mineral oil in the range of 2.7–3.3
(d) Cetyl alcohol in the range of 3.6–4.4
(e) Stearic acid in the range of 3.6–4.4
(f) Glycerol monostearate in the range of 2.7–3.3
(g) Coal tar topical solution in the range of 5.175–6.325
(h) Chamomile extract in the range of 0.9–1.1
(i) Methyl paraben in the range of 0.225–0.275
(j) Propyl paraben in the range of 0.09–0.11
(k) Triethanolamine in the range of 0.54–0.66
(l) Milk amino acids in the range of 2.25–2.75
(m) Mallow extract in the range of 0.9–1.1
(n) Tea tree solution in the range of 2.7–3.3
(o) Dimethicone in the range of 0.45–0.55
(p) Carbomer in the range of 3.6–4.4
(q) Glycerine in the range of 2.7–3.3
(r) Petrolatum in the range of 0.9–1.1
(s) Cetearyl alcohol in the range of 2.25–2.75
(t) Ceteareth 20 in the range of 2.25–2.75
(u) Polysorbate 20 in the range of 1.8–2.2
(v) F D and C Yellow #5 solution in the range of 0.045–0.055
(w) D and C red #33 solution in the range of 0.0045–0.055.

17. A method for treating psoriasis comprising topically administering to a human having psoriasis at least five percent coal tar and at least one percent herbal extract, said coal tar and herbal extract being present in a topically acceptable pharmaceutical body wash composition, spray composition and cream composition.

18. A method as claimed in claim 17 wherein said body wash composition consisting of the following ingredients in the following range of proportions:
(a) Water in the range of 40.19–49.12
(b) Sodium laureth sulphate in the range of 31.5–38.5
(c) Cocamide DEA in the range of 4.5–5.5
(d) Cocamidopropyl betaine in the range of 0.9–1.1
(e) Proylene glycol in the range of 0.27–0.33
(f) Citric acid in the range of 0.27–0.33
(g) Coal tar topical solution in the range of 5.4–6.6
(h) Sodium chloride in the range of 1.8–2.2
(i) Sodium layroyl sarcosinate in the range of 1.8–2.2
(j) Wheat germ oil in the range of 0.45–0.55
(k) Proteins (blends) in the range of 0.18–0.22
(l) Methylchloroisothiazolinone in the range of 0.045–0.055
(m) Mallow extract in the range of 0.9–1.1

(n) Rosemary oil in the range of 0.45 –0.55

(o) Eucalyptus oil in the range of 0.45 –0.55

(p) Carbomer in the range of 0.9–1.1.

19. A system for use in a psoriasis treatment as claimed in claim 18 wherein said spray composition consisting of the following ingredients in the following range of proportions:

(a) Water in the range of 21.573–26.367

(b) Alcohol in the range of 63–77

(c) Sodium Iodide in the range of 2.7–3.3

(d) Potassium iodide in the range of 1.35–1.65

(e) Sodium thiosulphate in the range of 0.027–0.033

(f) Mallow extract in the range of 0.9–1.1

(g) Rosemary oil in the range of 0.225–0.27

(h) Eucalyptus oil in the range of 0.225–0.27.

20. A system for use in a psoriasis treatment as claimed in claim 19 wherein said cream composition consisting of the following ingredients in the following range of proportions:

(a) Water in the range of 47.0205–27.4695

(b) Propylene glycol in the range of 3.6–4.4

(c) Mineral oil in the range of 2.7–3.3

(d) Cetyl alcohol in the range of 3.6–4.4

(e) Stearic acid in the range of 3.6–4.4

(f) Glycerol monostearate in the range of 2.7–3.3

(g) Coal tar topical solution in the range of 5.175–6.325

(h) Chamomile extract in the range of 0.9–1.1

(i) Methyl paraben in the range of 0.225–0.275

(j) Propyl paraben in the range of 0.09–0.11

(k) Triethanolamine in the range of 0.54–0.66

(l) Milk amino acids in the range of 2.25–2.75

(m) Mallow extract in the range of 0.9–1.1

(n) Tea tree solution in the range of 2.7–3.3

(o) Dimethicone in the range of 0.45–0.55

(p) Carbomer in the range of 3.6–4.4

(q) Glycerine in the range of 2.7–3.3

(r) Petrolatum in the range of 0.9–1.1

(s) Cetearyl alcohol in the range of 2.25–2.75

(t) Ceteareth 20 in the range of 2.25–2.75

(u) Polysorbate 20 in the range of 1.8–2.2

(v) F D and C Yellow #5 solution in the range of 0.045–0.055

(w) D and C red #33 solution in the range of 0.0045–0.055.

* * * * *